United States Patent
Takaku et al.

(10) Patent No.: US 6,495,675 B1
(45) Date of Patent: Dec. 17, 2002

(54) PHARMACEUTICAL COMPOSITION FOR TREATING OR PREVENTING INFLUENZA, AND NOVEL CAPPED OLIGONUCLEOTIDE

(75) Inventors: Hiroshi Takaku, Chiba (JP); Kin-ichiro Miura, Tokyo (JP); Toshifumi Hatta, Ibaraki (JP); Kazuyuki Takai, Chiba (JP); Masahide Ishikawa, Saitama (JP)

(73) Assignee: Chiba Institute of Technology, Chiba (JP)

( * ) Notice: Subject to any disclaimer, the term of this patent is extended or adjusted under 35 U.S.C. 154(b) by 0 days.

(21) Appl. No.: 09/603,378

(22) Filed: Jun. 26, 2000

Related U.S. Application Data

(63) Continuation-in-part of application No. PCT/JP98/05948, filed on Dec. 25, 1998.

(30) Foreign Application Priority Data

Dec. 26, 1997  (JP) ............................................... 9-369618

(51) Int. Cl.[7] ........................... C07H 21/04; C12N 5/00; C12N 5/02
(52) U.S. Cl. ...................... 536/24.5; 536/23.1; 435/375
(58) Field of Search ................................ 514/44; 435/6, 435/91.1, 325; 536/23.1, 24.1, 24.5

(56) References Cited

PUBLICATIONS

David B. Olsen et al., Elucidation of Basic Mechanistic and Kinetic Properties of Influenza Endonuclease Using Chemically Synthesized RNAs, The Journal of Biological Chemistry, vol. 271, No. 13 Mar. 29, 1996 pp. 7435–7439.*

S. Agrawal; Antisense oligonucleotides: towards clinical trials, TIBTECH Oct. 1996 vol. 14, pp. 376–387.*

Andrea D. Branch; A good antisense molecule is hard to find, TIBS Feb. 23, 1998 45–50.*

Alan M. Gewirtz et al., Facilitating oligonucleotide delivery: Helping antisense deliver on its promise, Proc. Natl. Acad. Sci. USA, vol. 93, pp. 3161–3163, Apr. 1996.*

Reimer Schlingensiepen, et al., Eds., Antisense–From Technology to Therapy Lab Manual and Textbook, Blackwell Science, vol. 6, pp. 252–261,(1997).

Reimer Schlingensiepen, et al., Eds., Antisense–From Technology to Therapy Lab Manual and Textbook, Blackwell Science, vol. 6, pp. 283–301,(1997).

Reimer Schlingensiepen, et al., Eds., Antisense–From Technology to Therapy Lab Manual and Textbook, Blackwell Science, vol. 6, pp. 322–331,(1997).

Sudhir Agrawal, Ed. Methods in Molecular Medicine, Antisense Therapeutics, Humana Press, Inc. , 47–56, (1996).

Sudhir Agrawal, Ed. Methods in Molecular Medicine, Antisense Therapeutics, Humana Press, Inc. , 57–85, (1996).

Sudhir Agrawal, Ed. Methods in Molecular Medicine, Antisense Therapeutics, Humana Press, Inc. , 109–119, (1996).

Sudhir Agrawal, Ed. Methods in Molecular Medicine, Antisense Therapeutics, Humana Press, Inc. , 121–141, (1996).

C. Cianci, et al, Differential effect of modified capped RNA substrates on influenza virus transcription, Virus Res., Jul. 1997, 50 (1): 65–75.

* cited by examiner

*Primary Examiner*—Andrew Wang
(74) *Attorney, Agent, or Firm*—Sughrue Mion, PLLC

(57) ABSTRACT

A pharmaceutical composition comprising a capped oligonucleotide capable of binding to a PB2 protein of an influenza virus RNA polymerase, and a pharmaceutically acceptable carrier or dilute, said capped oligonucleotide having a structure of the formula (I):

$$m^7GpppXpY \qquad (I)$$

wherein ppp is a triphosphate bridge, p is a monophosphate bridge, $m^7G$ is 7-methylguanosine group binding at 5' end thereof to said ppp, X is a 2'-O-methyl guanosine group or guanosine group, said 2'-O-methyl guanosine group or guanosine group binds at a 5' end thereof to said ppp, and at a 3' end thereof to said p, and Y is an oligoribonucleotide moiety binding at 5' end thereof to said p, and having 5 to 11 bases is disclosed. The pharmaceutical composition can inhibit a protein expression of an influenza virus.

4 Claims, 2 Drawing Sheets

F I G. 1

| Abbreviation | Sequence (5'→3') |
|---|---|
| 8-TOP | TAATACGACTCACTATAGAATACTC |
| 8-BTM | GAGTATTCTATAGTGAGTCGTATTA |
| 9-TOP | TAATACGACTCACTATAGAATACTCA |
| 9-BTM | TGAGTATTCTATAGTGAGTCGTATTA |
| 10-TOP | TAATACGACTCACTATAGAATACTCAA |
| 10-BTM | TTGAGTATTCTATAGTGAGTCGTATTA |
| 11-TOP | TAATACGACTCACTATAGAATACTCAAA |
| 11-BTM | TTTGAGTATTCTATAGTGAGTCGTATTA |
| 12-TOP | TAATACGACTCACTATAGAATACTCAAAC |
| 12-BTM | GTTTGAGTATTCTATAGTGAGTCGTATTA |
| 13-TOP | TAATACGACTCACTATAGAATACTCAAACT |
| 13-BTM | AGTTTGAGTATTCTATAGTGAGTCGTATTA |

PHARMACEUTICAL COMPOSITION FOR TREATING OR PREVENTING INFLUENZA, AND NOVEL CAPPED OLIGONUCLEOTIDE

CROSS REFERENCE TO RELATED APPLICATION

This is a continuation-in-part application of International Application No. PCT/JP98/05948 filed on Dec. 25, 1998, claiming a Convention priority date of Dec. 26, 1997 (Japanese Patent Application No. 9-369618).

BACKGROUND OF THE INVENTION

1. Field of the Invention

The present invention relates to a pharmaceutical composition for treating or preventing influenza, and a novel capped oligonucleotide.

2. Description of the Related Art

Influenza is extremely prevalent, repeatedly on a worldwide scale. Most people are infected by airborne germs. The influenza virus is highly infectious, and therefore, when a new subtype of the virus is generated, the prevailing scale thereof is enlarged beyond comparison with the infection of those suffering from the acquired immunodeficiency syndrome (AIDS).

The influenza virus belongs to orthomyxoviridae, and has a minus strand, i.e. a single strand RNA virus. The gene of the influenza virus is composed of eight segments. Among proteins encoded by the eight segmentation genes are hemagglutinin (HA) and neuraminidase (NA), which are two spikes on a surface of a virus particle and project from an envelope. There is also a segmentation gene encoding M2, one of the membrane proteins. On the surface of the virus particle exist two glycoproteins in the form of spikes embedded in a lipid bilayer (envelope) stemming from a host. Furthermore, there is another membrane protein, M1. The segmentation gene encoding M2 is also contained in the virus gene. A ribonucleoprotein (RNP) complex is located at the center of the virus, and composed of the gene RNA, three RNA polymerase subunits (PB1, PB2, and PA), and a nucleoprotein (NP). The segments encoding the proteins, PB1, PB2, PA, and NP, are also contained in the virus gene. A non-structural protein is synthesized from the 8th segmentation gene.

The influenza viruses are classified into three types, A, B, and C, on the basis of the differences in serotypes of the nucleoprotein (NP) and the membrane protein M2. The above three proteins PB1, PB2, and PA in the influenza virus are subunits which constitute an RNA polymerase. Amino acid sequences of the RNA polymerase are conserved in the influenza A, B, C or a mutant thereof. The RNA polymerase catalyzes a synthesizing reaction of RNA, an addition reaction of poly A, a restriction reaction of a cap, or the like. In particular, PB1 participates in the synthesizing reaction of RNA, and PB2 recognizes an mRNA cap structure of a host cell, and cleaves mRNA. PA has a role in transcription and elongation reactions. NP is a polynucleotide-binding protein non-specific to a base sequence. An RNA in an NP-RNA complex forms a double strand or a helix, and is important for a transcriptional reaction of a virus. Further, PB2, PB1, PA, NP, and NS are synthesized in an initial stage of the infection, respectively.

Of the influenza viruses, the influenza A virus undergoes a substantial change in antigenecity, and prevails above all others. In view of an acute infectivity thereof, the influenza A virus is most malignant. As an antiviral agent for the influenza A virus, amantadine or rimantadine are known, but these cannot cope with mutants and have strong side effects. Thus, a medicament exhibiting a satisfactorily antiviral activity has not been developed. Further, a treatment with an inactivated vaccine has been attempted, but there is a difference between the inactivated vaccine and an antibody generated by a natural infection, and thus there are fewer people to whom the vaccine is administered. Further, the vaccine does not have a sufficient effect in a sustainability of producing antibodies, and thus cannot completely prevent the spread of infection. The effect of the inactivated vaccine can not be sustained for a long period, and thus the development of an attenuated vaccine is still desired. Therefore, there exists no vaccine that can be put to practical use. A difficult problem is the substantial changes in viral antigenecity, and this is one of causes of the delay in the development of the vaccine.

Recently, the development of a gene-analyzing technique has made it possible to easily determine a mutant gene sequence. As an antiviral agent for the influenza viruses encountering considerable mutations, it would be suitable to use a method wherein a gene is a target, e.g., an antisense oligonucleotide method, such as an antisense DNA method.

In the antisense oligonucleotide method, an oligonucleotide having a base sequence complementary to that of a target gene is used to inhibit a transcription, splicing, or translation of the target gene, at an mRNA level. This technique can specifically prevent the expression of viral proteins, in a mechanism different from a medicament [S. T. Crooke, Therapeutic Applications of Oligonucleotides, Springer-Verlag, (1995)].

However, it would be difficult to completely prevent the expression of the viral proteins by the antisense oligonucleotide method, because a main target in the antisense oligonucleotide method is a viral mRNA, which is an intermediate product. More particularly, a synthesizing rate of the viral proteins from the viral mRNAs is very rapid in a cell infected with an influenza virus, and thus a part of the viral proteins may be produced before the antisense nucleotide functions to the targent mRNA. This would lead to an investigation of the potentiality of an antiviral agent utilizing a decoy RNA against a final product, i.e., a viral protein, such as a viral RNA polymerase, which plays an important role in the proliferation of viruses.

For example, the PB2 protein, one of the influenza virus RNA polymerases, utilizes a part of the 5' end of a host cell mRNA, when an mRNA is transcribed from an influenza viral RNA (vRNA) in an initial stage of the infection with the influenza virus. More particularly, the PB2 protein recognizes and binds to an oligoribonucleotide moiety of a first 10 to 13 base sequence containing a cap structure located at the 5' end of the mRNA of the infected host cell. Thereafter, the rest of the mRNA is cleaved out, and a complementary chain is elongated after the bound first 5' terminal oligoribonucleotide moiety, using the vRNA having genetic information of the influenza virus as a template, to generate an mRNA having the genentic information of the influenza virus.

The present inventors conducted in vivo experiments using similar oligoribonucleotides (synthesized mRNAs), and surprisingly, found that oligoribonucleotides (synthesized mRNAs) having 10 to 12 bases (nucleotides) effectively inhibit the RNA elongation reaction. The present inventors also found that the in vitro results obtained by D. Y. Thomas, et al cannot be applied to an in vivo experiment. Further, the present inventors found that oligoribonucleotides having 8 to 9 bases effectively inhibit the RNA elongation reaction in vivo.

The present invention is based on the above findings.

SUMMARY OF THE INVENTION

Accordingly, the object of the present invention is to provide a method or a pharmaceutical composition for treating or preventing an influenza virus.

Another object of the present invention is to provide a novel oligoribonucleotides.

Other objects and advantages of the present invention will be apparent from the following description.

In accordance with the present invention, there is provided a pharmaceutical composition comprising a capped oligonucleotide capable of binding to a PB2 protein of an influenza virus RNA polymerase, and a pharmaceutically acceptable carrier or dilute, the capped oligonucleotide having a structure of the formula (I):

$m^7GpppXpY$ (I)

wherein ppp is a triphosphate bridge, p is a monophosphate bridge, $m^7G$ is 7-methylguanosine group binding at the 5' end thereof to the ppp, X is 2'-O-methyl guanosine group or guanosine group, the 2'-O-methyl guanosine group or guanosine group binds at the 5' end thereof to the ppp, and at the 3' end thereof to the p, and Y is an oligoribonucleotide moiety binding at the 5' end thereof to the p, and having 5 to 11 bases.

In accordance with the present invention, there is also provided a method for treating or preventing influenza, comprising administering to a subject in need thereof a capped oligonucleotide of the formula (I) in an amount effective in treating or preventing influenza.

Further, the present invention relates to a capped oligonucleotide of the formula (I) wherein Y is an oligoribonucleotide moiety consisting of the base sequence of SEQ ID NO: 4 or SEQ ID NO: 5.

Still further, the present invention relates to a pharmaceutical composition comprising the capped oligonucleotide of the formula (I) wherein Y is an oligoribonucleotide moiety consisting of the base sequence of SEQ ID NO: 4 or SEQ ID NO: 5, and a pharmaceutically acceptable carrier or dilute.

Still further, the present invention relates to a method for treating or preventing influenza, comprising administering to a subject in need thereof the capped oligonucleotide of the formula (I) wherein Y is an oligoribonucleotide moiety consisting of the base sequence of SEQ ID NO: 4 or SEQ ID NO: 5 in an amount effective in treating or preventing influenza.

BRIEF DESCRIPTION OF DRAWINGS

FIG. 1 is a Table listing base sequences of DNA templates for synthesizing capped oligonucleotides in Example 1 (SEQ ID NO:7–18).

DESCRIPTION OF THE PREFERRED EMBODIMENTS

Figure 2:
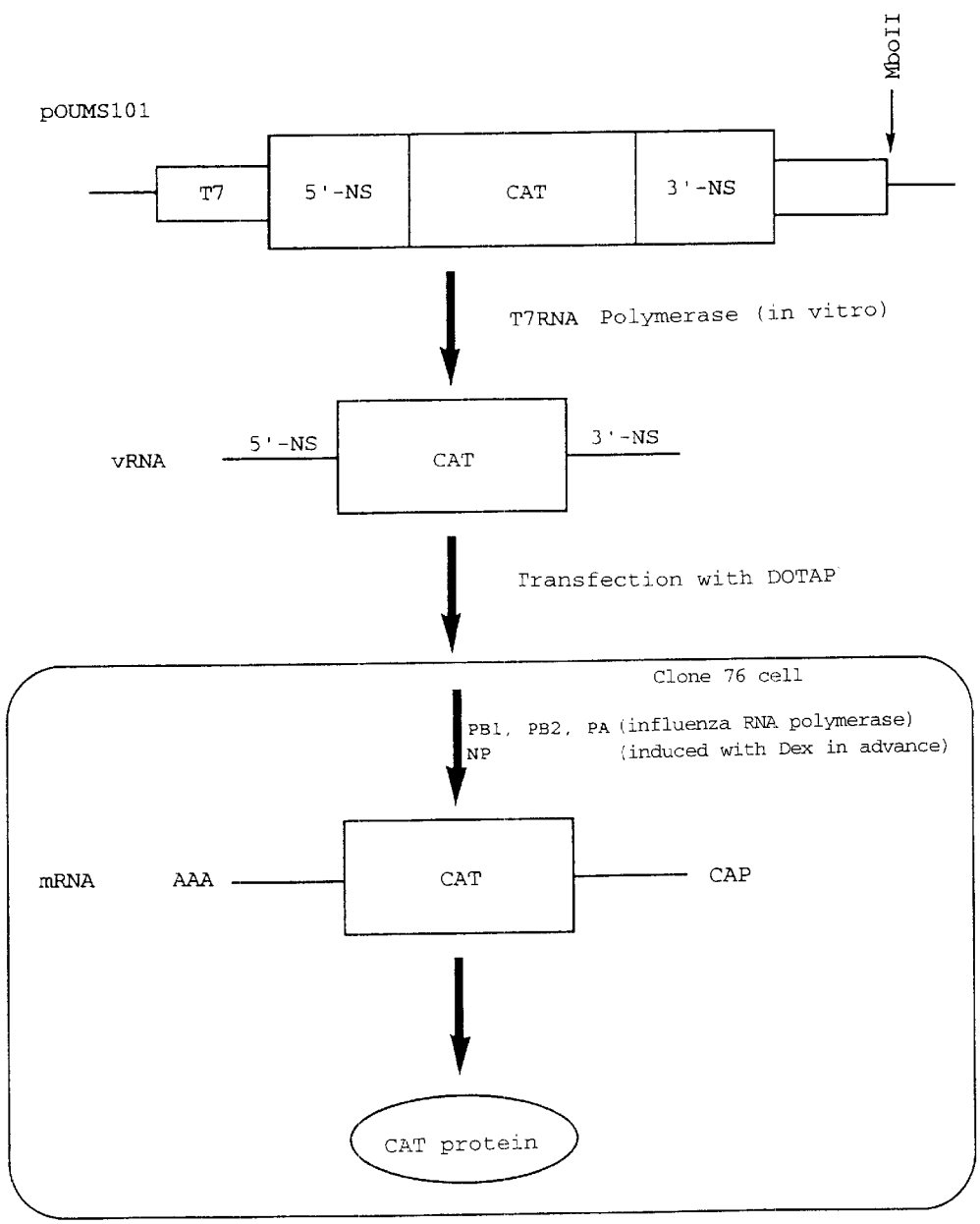
FIG. 2 illustrates an outline of the procedures of the experiment in Example 2, i.e., an experiment for an inhibitory activity of a CAT protein expression.

The present invention will be explained in detail hereinafter.

The term "influenza virus" as used herein includes influenza A, influenza B, and influenza C, and mutants thereof.

The term "PB2 protein" as used herein means one of the three subunits (i.e., the PB1 protein, the PB2 protein, and the PA protein) constituting the influenza virus RNA polymerase. Therefore, the PB2 protein of the influenza virus includes PB2 proteins of the influenza A, influenza B, and influenza C, and PB2 proteins of mutants thereof.

The capped oligonucleotide of the formula (I) which may be used as an active ingredient in the pharmaceutical composition for treating or preventing influenza according to the present invention contains a cap structure ($m^7GpppX-$) of an mRNA at the 5' end thereof. The cap structure has a structure of the formula (Ia):

$m^7GpppGm-$ (Ia)

wherein ppp and $m^7G$ have the meanings as above, and Gm is 2'-O-methyl guanosine group binding at the 5' end thereof to the ppp, or the formula (Ib):

$m^7GpppG-$ (Ib)

wherein ppp and $m^7G$ have the meanings as above, and G is guanosine group binding at the 5' end thereof to the ppp. The cap structure of the formula (Ia) is preferable.

The chemical structure of the cap structure of the formula (Ia) is as follows:

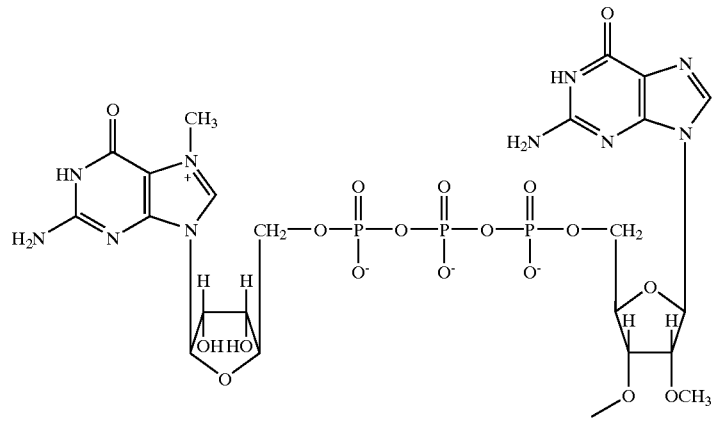

The chemical structure of the cap structure of the formula (Ib) is as follows:

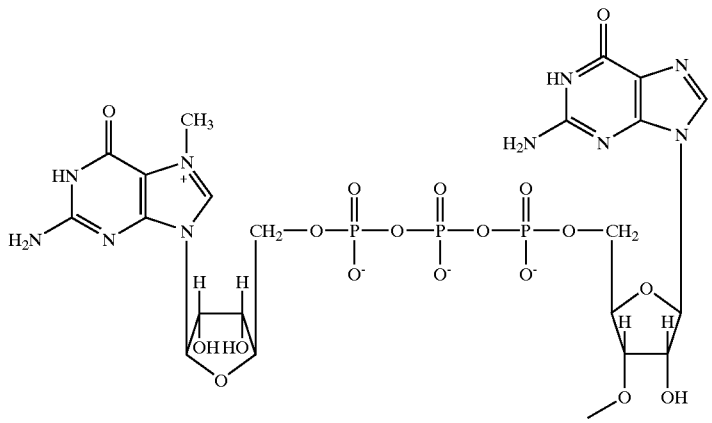

In the capped oligonucleotide of the formula (I), the oligoribonucleotide moiety Y has 5 to 11 bases (nucleotides), preferably 7 to 11 bases (nucleotides), more preferably 9 to 11 bases (nucleotides). If the oligoribonucleotide moiety Y has more than 11 bases, the capped oligonucleotide of the formula (I) or a part thereof may be used as a primer for synthesizing an influenza viral mRNA, and the synthesis may start. If the oligoribonucleotide moiety Y has less than 5 bases, the capped oligonucleotide of the formula (I) cannot always bind to the PB2 protein.

In the capped oligonucleotide of the formula (I), the base sequence of the oligoribonucleotide moiety Y is not particularly limited, so long as it can bind to the PB2 protein, the subunit of the influenza virus RNA polymerase. The oligoribonucleotide moiety Y may have a naturally occurring base sequence, or an artificially designed base sequence.

In the capped oligonucleotide of the formula (I), the oligoribonucleotide moiety Y preferably has the base sequence of one of SEQ ID NO: 1 to 5.

In the capped oligonucleotide of the formula (I), internucleotide bonds between nucleotides (including the triphosphate bridge between $m^7G$ and ppp, and the monophosphate bridge between X and Y) may be independently a phosphodiester bond or a modified phosphodiester bond. The modified phosphodiester may be, for example, a phosphorothioate type bond wherein one of two non-crosslinked oxygen atoms in the phosphodiester bond is replaced with a sulfur atom; or a phosphorodithioate type bond wherein each of two non-crosslinked oxygen atoms in the phosphodiester bond is replaced with a sulfur atom. The capped oligonucleotide of the formula (I) may contain one or more modified phosphodiester bonds as above in one or more internucleotide bonds. The modified phosphodiester bond is preferable as the internucleotide bond, from the standpoints of the specificity in molecular recognition, a stability of the double-stranded chain, a resistance to a nuclease, a penetrating property through a cell membrane, a low cytotoxicity, a moderate metabolizability, an easy procedure for preparation, and so on. Further, the phosphorothioate type bond is more preferable from the standpoint of a stability in a living body. It is particularly preferable that not less than half, or in particular all, of the internucleotide bonds are the modified phosphodiester bonds, in particular the phosphorothioate type bonds.

Specifically, the capped oligonucleotides of the formula (I) which may be used as an active ingredient in the pharmaceutical composition for treating or preventing influenza according to the present invention may be the oligonucleotides of the formula (I) wherein the cap structure has the structure of the formula (Ia) or (Ib), and the oligoribonucleotide moiety Y has the base sequence of one of SEQ ID NO: 1 to 5. Of the above capped oligonucleotides, the oligonucleotides of the formula (I) wherein the cap structure has the structure of the formula (Ia) or (Ib), and the oligoribonucleotide moiety Y has the base sequence of SEQ ID NO: 4 or 5 are novel compounds.

The capped oligonucleotides of the formula (I) are effective against the influenza A virus, influenza B virus, and influenza C virus, and mutants thereof, particularly effective against the influenza A virus.

The capped oligonucleotides of the formula (I) which may be used as an active ingredient in the pharmaceutical composition for treating or preventing influenza according to the present invention may be prepared in accordance with methods which are in themselves known, for example, by a chemically synthesizing method, a method using a capping and methylating enzyme derived from vaccinia virus, a method using a T7 RNA polymerase, or the like.

For example, the capped oligonucleotides having the cap structure $m^7GpppGm$ at the 5' end may be prepared by the following procedures in accordance with the method using a T7 RNA polymerase. A plus strand and a minus strand of a double-stranded DNA containing a desired base sequence and a T7 promoter sequence are prepared by an automated DNA/RNA synthesizer in accordance with a phosphoramidite method. Then, a transcriptional reaction of a T7 RNA polymerase is carried out, using a template of a double-stranded DNA composed of the resulting plus and minus strands in the conventional reaction conditions except that $m^7GpppGm$ is added, to thereby form the capped oligonucleotide. When $m^7GpppG$ is used instead of $m^7GpppGm$, the capped oligonucleotides having the cap structure $m^7GpppG$ at the 5' end may be prepared.

The cell membrane-penetrating property of the capped oligonucleotides of the formula (I) may be enhanced by methods which are in themselves known. For example, there may be mentioned a method of embedding the capped oligonucleotide in a liposome [M. Mozuno et al., Cancer Res., 50, 7826 (1991)], a method of introducing cholesterol into a terminus of the oligonucleotide [B. Oberhauer and E. Wagner, Nucleic Acids Res., 20, 533 (1993)], a method of non-covalently binding the oligonucleotide to a transferrin-poly-L-lysine complex [G. Citro, Proc. Natl. Acad. Sci. USA, 89, 7031 (1992)], and taking up the oligonucleotide into a hepatocyte expressing a galactose receptor or into a cancer cell expressing a transferrin receptor, or a method of augmenting an uptake into a cell and a transfer into a nucleus by adding a cationic lipid, such as lipofectin, to the target cell together with the oligonucleotide interacted therewith, to thereby enhance an antisense effect [M. Chiany et al., J. Biol. Chem., 266, 18162 (1991)].

An antiviral effect of the capped oligonucleotides of the formula (I) which may be used as an active ingredient in the pharmaceutical composition for treating or preventing influenza according to the present invention can be confirmed, for example, by an expression amount of chloramphenicol acetyltransferase (hereinafter referred to as CAT) in clone cells (hereinafter referred to as 76 cells) [Y. Nakamura, K. Oda and S. Nakada, J. Biochem., 110, 395 (1991)] of a C127 cell strain, using plasmid pOUMS101 [Proc. Natl. Acad. Sci. USA, vol. 88, pp. 5369–5373 (1991)], and 76 cells.

The plasmid pOUMS101 is prepared by inserting, downstream of a phage T7 RNA polymerase promoter, a DNA fragment which is prepared by substituting a CAT gene for a protein coding region in the 8th segmentation gene of influenza virus PR8 strain and contains a base sequence of 13 base pairs in a 5'-upstream region in the protein coding region in the 8th segmentation gene and a base sequence of 12 base pairs in a 3'-downstream region in the protein coding region in the 8th segmentation gene. Further, in the 76 cells, an expression of the RNA polymerases (PB1, PB2, and PA), and the NP protein of the influenza A virus (A/PR/8/34) is induced by adding dexamethasone, which is a steroid hormone.

More particularly, a CAT gene-containing RNA (hereinafter referred to as vRNA) is produced in vitro, using a T7 RNA polymerase and the plasmid pOUMS101 as a template. The capped oligonucleotide to be examined is added to the 76 cells wherein expressions of PB1, PB2, PA, and NP proteins have been induced by adding dexamethasone. When the capped oligonucleotide is taken into the cell, vRNA prepared as above is added to the 76 cells and taken thereinto. If the capped oligonucleotide to be examined does not bind to the PB2 protein in the cell, the cleavage of the cap normally proceeds. Therefore, vRNA is transcribed and replicated by the action of the RNA polymerases (PB1, PB2, and PA) and the NP protein which are expressed in the cell, and a CAT is expressed. On the contrary, if the capped oligonucleotide to be examined binds to the PB2 protein in the 76 cells, the PB2 protein cannot cleave the capped site of the host cell mRNA. As a result, the transcription from vRNA to mRNA is inhibited, and thus an amount of CAT expressed is also inhibited. Accordingly, an antiviral activity of the capped oligonucleotide to be examined can be evaluated by measuring the amount of CAT expressed in the 76 cells.

The action of the capped oligonucleotides of the formula (I) which may be used as an active ingredient in the pharmaceutical composition for treating or preventing influenza according to the present invention is presumed, but by no means limited to the following presumption, for example, that if the capped oligonucleotides of the formula (I) exist in a cell, they bind to the PB2 proteins which are a subunit of the RNA polymerase, and thus an mRNA synthesis by the RNA polymerase can be inhibited.

In the conventional antisense nucleotide method, an intermediate product, a viral mRNA, is a target. On the contrary, the target of the capped oligonucleotides of the formula (I) is a final product, a viral RNA polymerase, and therefore, a viral proliferation can be more effectively inhibited.

EXAMPLES

The present invention now will be further illustrated by, but is by no means limited to, the following Examples.

Example 1

In accordance with the method using a T7 RNA polymerase, seven capped oligonucleotides of the formula (I), which may be used as the active ingredient in the pharmaceutical composition of the present invention for treating or preventing influenza, and a capped oligonucleotide for comparison were synthesized as follows:

(1) Design of Capped Oligonucleotides

A capped oligonucleotide (hereinafter referred to as Gm8) having a cap structure of the formula (Ia) and an oligoribonucleotide moiety Y of the base sequence of SEQ ID No: 1 (the number of bases=7);

a capped oligonucleotide (hereinafter referred to as Gm9) having a cap structure of the formula (Ia) and an oligoribonucleotide moiety Y of the base sequence of SEQ ID No: 2 (the number of bases=8);

a capped oligonucleotide (hereinafter referred to as Gm10) having a cap structure of the formula (Ia) and an oligoribonucleotide moiety Y of the base sequence of SEQ ID No: 3 (the number of bases=9);

a capped oligonucleotide (hereinafter referred to as Gm11) having a cap structure of the formula (Ia) and an oligoribonucleotide moiety Y of the base sequence of SEQ ID No: 4 (the number of bases=10);

a capped oligonucleotide (hereinafter referred to as Gm12) having a cap structure of the formula (Ia) and an oligoribonucleotide moiety Y of the base sequence of SEQ ID No: 5 (the number of bases=11);

a capped oligonucleotide (hereinafter referred to as Gm13) having a cap structure of the formula (Ia) and an oligoribonucleotide moiety Y of the base sequence of SEQ ID No: 6 (the number of bases=12);

a capped oligonucleotide (hereinafter referred to as G8) having a cap structure of the formula (Ib) and an oligoribonucleotide moiety Y of the base sequence of SEQ ID No: 1 (the number of bases=7); and a capped oligonucleotide (hereinafter referred to as Gm12 (S)) having a cap structure of the formula (Ia), and an oligoribonucleotide moiety Y of the base sequence of SEQ ID No: 5 (the number of bases=11) wherein all of the internucleotide bonds in the oligoribonucleotide moiety Y are a phosphorothioate type bond; were synthesized.

Of these capped oligonucleotides, the seven capped oligonucleotides Gm8, Gm9, Gm10, Gm11, Gm12, G8 and Gm12(S) were the capped oligonucelotides which may be used as the active ingredient in the pharmaceutical composition of the present invention for treating or preventing influenza, and Gm13 was the capped oligonucleotide for comparison. The sequences of the capped oligonucleotides are shown in FIG. 1. In Table 1, "A", "G", "C", "U", and "$m^7G$" denote adenosine, guanosine, cytidine, uridine, and 7-methylguanosine, respectively. Further, "p" denoted a phosphodiester bond, "m" immediately after "G" denotes that the 2-hydroxyl group of a ribose in G (guanosine) is methylated, and "s" denotes that an internucleotide bond is a phosphorothioate type bond.

TABLE 1

| Abbreviation | Sequence (5'→3') |
|---|---|
| Gm8 | $m^7G_{ppp}$GmAAUACUC |
| Gm9 | $m^7G_{ppp}$GmAAUACUCA |
| Gm10 | $m^7G_{ppp}$GmAAUACUCAA |
| Gm11 | $m^7G_{ppp}$GmAAUACUCAAA |
| Gm12 | $m^7G_{ppp}$GmAAUACUCAAAC |
| G8 | $m^7G_{ppp}$G AAUACUC |

TABLE 1-continued

| Abbreviation | Sequence (5'→3') |
| --- | --- |
| Gm12 (S) (for comparison) | m$^7$G$_{ppp}$GmAsAsUsAsCsUsCsAsAsAsC |
| Gm13 | m$^7$G$_{ppp}$GmAAUACUCAAACU |

(2) Preparation of Template DNAs for Synthesis of Capped Oligonucleotides

Base sequences of the synthesized oligonucleotides are shown in FIG. 1. In FIG. 1, "8-TOP" (SEQ ID NO: 7) and "8-BTM" (SEQ ID NO: 8) denote a template DNA for the capped oligonucleotide Gm8 or the capped oligonucleotide G8; "9-TOP" (SEQ ID NO: 9) and "9-BTM" (SEQ ID NO: 10) denote a template DNA for the capped oligonucleotide Gm9; "10-TOP" (SEQ ID NO: 11) and "10-BTM" (SEQ ID NO: 12) denote a template DNA for the capped oligonucleotide Gm10; "11-TOP" (SEQ ID NO: 13) and "11-BTM" (SEQ ID NO: 14) denotes a template DNA for the capped oligonucleotide Gm11; "12-TOP" (SEQ ID NO: 15) and "12-BTM" (SEQ ID NO: 16) denote a template DNA for the capped oligonucleotide Gm12; and "13-TOP" (SEQ ID NO: 17) and "13-BTM" (SEQ ID NO: 18) denote a template DNA for the capped oligonucleotide Gm13, respectively. In the abbreviations of the oligonucleotides shown in FIG. 1, "TOP" denotes a plus trand of a double-stranded DNA template, and "BTM" denotes a minus strand of a double-stranded DNA as a template.

Twelve oligonucleotides shown in FIG. 1 were synthesized, using a DNA automated synthesizer (Applied Biosystems Model 392) in accordance with a program for a normal DNA. That is, oligonucleotides were synthesized in accordance with a phosphoramidite method using a solid phase column (1 µmol scale; Cruachem, United Kingdom) and reagents for DNA synthesis (Cruachem, United Kingdom), and then, cut from the column and deprotected in accordance with the conventional method [A. Chollet & E. H. Kawashima, Nucleic Acids Res., 13, 1529 (1985)]. An amount of 1/500 (about 4 µg) of each of the resulting oligonucleotides was applied to a 20% polyacrylamide gel electrophoresis containing 7 M urea. The electrophoresis was carried out at a constant voltage of 150 V for 1.5 hours. After the electrophoresis was completed, the gel was stained with methylene blue to confirm that each of the synthesized oligonucleotides had a predetermined strand length.

As to the confirmed oligonucletides, ⅓ to ½ (about 1.2 mg) of the remaining oligonucletides was subjected to the 20% polyacrylamide gel electrophoresis containing 7 M urea, which electrophoresis was used for cutting out and purification. The electrophoresis was carried out at a constant voltage of 200 V for 6 hours. After the electrophoresis was completed, the gel was removed from a gel plate, covered in a wrap, and irradiated with ultraviolet light. Bands having the predetermined strand length were marked, and the marked gels were then divided into small pieces with a sterilized cutter, and collected into a 1.5 ml volume of sample tubes. To the tubes, 0.4 ml of a solution containing 10 mM Tris-HCl (pH 7.5) and 1 mM-EDTA was added, and then DNAs were extracted from the gel pieces to the solutions with shaking at 37° C. for 3 to 12 hours. The extracts were collected, and extracted with phenol/chloroform to remove acrylamide. Thereafter, an ethanol precipitation was carried out to purify the oligonucletides. The yields of the oligonucletides were 0.3 to 0.6 mg. Each of the resulting oligonucletides (about 0.5 µg) was applied to the polyacrylamide gel electrophoresis containing 7 M urea, and then the gel was stained with ethidium bromide. Each of the oligonucletides showed a single band.

(3) Preparation of Capped Oligonucleotides

A template DNA was prepared by mixing 0.3 µg of the oligonucleotide 8-TOP obtained in Example 1(2) and 0.3 µg of the oligonucleotide 8-BTM obtained in Example 1(2) in a total volume of 2 µl, annealing at 95° C. for 3 minutes, and cooling to room temperature to form a complementary strand.

To 2 µl of the resulting template DNA, a 5× concentrated buffer for transfer [0.2 M HEPES-KOH/0.08 M MgCl$_2$/0.2 M KCl (pH 8.1)], 100 mM ATP, 100 mM CTP, 100 mM-UTP, 0.03 mg of cap-1 substrate (m$^7$$_{ppp}$Gm), 250 mM dithiothreitol (DTT), 100 mM Spermidine, 20 mg/ml bovine serum albumin (BSA), 40 unit/µl ribonuclease inhibitor, and 20 unit/µl-T7 RNA polymerase were added (total volume=50 µl), and then a transcriptional reaction was carried out at 37° C. for 2 hours.

After the transcriptional reaction was completed, 50 µl of phenol/chloroform was added to perform an extraction. A supernatant was carefully recovered and precipitated with ethanol. To confirm whether or not the transcriptional reaction was successfully carried out, 1/100 of the resulting product was applied to a 20% polyacrylamide gel electrophoresis containing 7 M urea. The electrophoresis was carried out at a constant voltage of 100 V for 2 hours. After the electrophoresis was completed, the gel was stained with methylene blue to confirm that the transferred capped oligonucleotide was the capped oligonucleotide Gm8 having a predetermined strand length.

After the strand length was confirmed, all of the remaining product was applied to the 20% polyacrylamide gel electrophoresis containing 7 M urea, which electrophoresis was used for cutting out and purification. The electrophoresis was carried out at a constant voltage of 200 V for 6 hours. After the electrophoresis was completed, the gel was removed from a gel plate, covered with a wrap, and irradiated with ultraviolet light, and then a band having the predetermined strand length was marked. The marked gel was divided into small pieces with a sterilized cutter, and collected into a 1.5 ml volume of sample tube. To the tube, 0.4 ml of a solution containing 10 mM Tris-HCl (pH 7.5) and 1 mM EDTA was added, and then RNA was extracted from the gel pieces to the solution with shaking at 37° C. for 3 to 12 hours. The extract was collected, and extracted with phenol/chloroform to remove acrylamide. Thereafter, an ethanol precipitation was carried out to purify the capped oligonucleotide. The yield of the resulting capped oligonucleotide Gm8 was 0.04 mg. About 0.5 µg of the resulting purified capped oligonucleotide was applied to the polyacrylamide gel electrophoresis containing 7 M urea, and then the gel was stained with ethidium bromide. The oligonucletides showed a single band.

The same procedures were repeated, except that the other oligonucleotides shown in FIG. 1 were selected and used instead of the oligonucleotides 8-TOP and 8-BTM, to prepare the capped oligonucleotide Gm9, the capped oligonucleotide Gm10, the capped oligonucleotide Gm11, the capped oligonucleotide Gm12, and the capped oligonucleotide Gm13.

Further, the same procedure was repeated, except that the cap substrate (m$^7$G$_{ppp}$G) was used instead of the cap-1 substrate (m$^7$G$_{ppp}$Gm), to prepare the capped oligonucleotide G8.

In accordance with a similar procedure, the capped oligonucleotide Gm12(S) was prepared.

Example 2

In this Example, an antiviral effect of the capped oligonucleotides was evaluated in accordance with an inhibitory activity test of a CAT protein expression.

(1) A System for Evaluating Capped Oligonucleotides

In this Example, the inhibitory activity test of CAT protein expression was carried out using plasmid pOUMS101 [Proc.

Natl. Acad. Sci. USA, vol. 88, pp. 5369–5373 (1991)] and clone cells (hereinafter referred to as 76 cells) of a C127 cell strain [Y. Nakamura et al., J. Biochem., 110, 395 (1991)]. In the 76 cells, an expression of the RNA polymerases (PB1, PB2, and PA) of influenza A virus (A/PR/8/34) and the NP protein were induced by adding dexamethasone. The plasmid pOUMS101 is prepared by inserting, downstream of a phage T7 RNA polymerase promoter, a DNA fragment which is prepared by substituting a CAT gene for a protein coding region in the 8th segmentation gene of influenza virus PR8 strain and contains a base sequence of 13 base pairs in a 5'-upstream region in the protein coding region in the 8th segmentation gene and a base sequence of 12 base pairs in a 3'-downstream region in the protein coding region in the 8th segmentation gene. In the 76 cells, the CAT protein can be produced by transfection of a negative strand RNA (containing a CAT gene) synthesized in vitro using the plasmid pOUMS101 as a template. The outline of the procedures in this Example is shown in FIG. 2.

(2) Preparation of a Negative Strand RNA Containing a CAT Gene

The plasmid pOUMS101 was prepared in accordance with a conventional method described in Proc. Natl. Acad. Sci. USA, vol. 88, pp. 5369–5373 (1991). A partial structure of the plasmid pOUMS101 is schematically shown in FIG. 2. In FIG. 2, "CAT" denotes a CAT gene encoding a CAT protein, "T7" denotes a phage T7 RNA polymerase promoter, "5'-NS" denotes a base sequence of 13 base pairs in a 5'-upstream region in the protein non-coding region in the 8th segmentation gene of the influenza virus PR8 strain, "3'-NS" denotes a base sequence of 12 base pairs in a 3'-downstream region in the protein non-coding region in the 8th segmentation gene of the influenza virus PR8 strain, "CAP" denotes a cap structure of mRNA, and "CAT protein" denotes a CAT protein. The plasmid pOUMS101 contains an MboII recognition site at the 3'-downstream side of the 3'-NS region.

The resulting plasmid pOUMS101 (10 µg) was digested and linearized with 32 units of a restriction enzyme MboII (TOYOBO). After digestion, the reaction mixture was extracted with phenol/chloroform (1:1), and then an upper layer (aqueous layer) was carefully recovered and precipitated with ethanol. Then, 1/15 amount (about 0.6 µg) thereof was applied to a 0.8% agarose gel electrophoresis (a constant voltage of 50 V; 1.5 hours) to confirm the digestion. Using the resulting linearized plasmid pOUMS101 (10 µg) as a template and a T7 RNA polymerase (TOYOBO), a negative strand RNA containing a CAT gene (vRNA shown in FIG. 2) was synthesized in accordance with a manual attached thereto. The reaction mixture was extracted with phenol/chloroform (1:1), and then an upper layer (aqueous layer) was carefully recovered and precipitated with ethanol. Then, a part (1/100) of the resulting RNA was applied to a polyacrylamide gel electrophoresis containing 7 M urea to confirm a product having a predetermined strand length.

(3) Measurement of an Inhibitory Activity of a CAT Protein Expression 76 cells prepared in accordance with a method described in Y. Nakamura et al., J. Biochem., 110, 395 (1991) were cultured in 5 ml of a Dulbecco's MEM medium (hereinafter referred to as D-MEM) (Nissui Seiyaku) containing 10% inactivated fetal bovine serum (inactivation was carried out by heating at 56° C. for 30 minutes) to a 50 to 60% confluent. After the medium was removed, 3 ml of a medium prepared by diluting $10^{-3}$ M dexamethasone (Dex shown in FIG. 2) (Sigma) with D-MEM to 1000-fold (final concentration=$10^{-6}$ M) was added to the confluent 76 cells. After being cultured for 24 hours, the cells were thoroughly washed with phosphate buffered saline [hereinafter referred to as PBS (−)] so that no fetal bovine serum remained. To the 76 cells, 2.5 ml of serum-free D-MEM (containing HEPES and bovine serum albumin) containing each of capped oligonucleotides (0.03 µM or 0.3 µM) prepared in Example 1 and 5 µg/ml of N-[1-(2,3-dioleoyloxy)propyl]-N,N,N-trimethylammonium methylsulfate (DOTAP; Boehringer Mannheim) as a transfection reagent.

After being cultured further for 4 hours, the cells were washed with PBS (−). To the cells, serum-free D-MEM (containing HEPES and bovine albumin) containing 100 ng of the negative strand RNA containing the CAT gene prepared in Example 2(2) and 5 µg/ml of DOTAP was added. After being cultured for 4 hours, DOTAP was removed. The cells were washed with PBS (−) and cultured in a D-MEM containing 10% inactivated fetal bovine serum for 20 hours. After the cells were collected and ruptured, a total mass of the obtained proteins was measured in accordance with a Bradford method. Further, in accordance with ELISA using an anti-CAT antibody labeled with Digoxigenin (DIG) (Anti-CAT-DIG; Boehringer Mannheim) (CAT-ELISA), an amount of the CAT protein expressed in the cells was measured. That is, each of an amount of DIG-labeled anti-CAT antibodies reacted with the CAT proteins expressed in 76 cells was measured using anti-DIG antibodies labeled with peroxidase, and then each of an amount of the CAT protein expressed was compared.

The results are shown in Table 2. The figures for the inhibitory activity (%) of the CAT protein expression shown in Table 2 were calculated on the basis of the amount of the CAT protein expression without adding a capped oligonucleotide. In other words, the inhibitory activity is given as the percentage of inhibition of the CAT protein expression obtained by adding the capped oligonucleotide in comparison with the standard where a capped oligonucleotide is not added. Therefore, a high figure (close to 100%) means a strong inhibition of the CAT protein expression, i.e., an acute antiviral activity, whereas a low figure (close to 0%) means a weak inhibition of the CAT protein expression.

As shown in Table 2, the capped oligonucleotide Gm13 for comparison exhibited a weak inhibition of CAT protein expression. In particular, it showed little inhibition of CAT protein expression in the high dose (0.3 µM). To the contrary, each of the capped oligonucleotides which may be used as the active ingredient in the pharmaceutical composition of the present invention for treating or preventing influenza exhibited a significant inhibition of CAT protein expression (50% or more).

As apparent from the comparison on the inhibition of CAT protein expression among the capped oligonucleotide Gm8, the capped oligonucleotide Gm9, the capped oligonucleotide Gm10, the capped oligonucleotide Gm11, and the capped oligonucleotide Gm12, no correlation between the number of bases and the inhibition was observed. In the range of 8 to 12 bases, the capped oligonucleotides exhibited a significant inhibition of CAT protein expression.

Further, as apparent from the comparison between the capped oligonucleotide Gm8 and the capped oligonucleotide G8, both of the capped oligonucleotides exhibited a significant inhibition of the CAT protein expression, and the inhibition of the capped oligonucleotide Gm8 was higher than that of the capped oligonucleotide G8. This indicates that the inhibition of the CAT protein expression can be increased by a methylation of a 2-hydoxyl group in ribose of the first nucleotide.

Furthermore, as apparent from the comparison between the capped oligonucleotide Gm12 and the capped oligonucleotide Gm12(S), a phosphothioate bond can increase the inhibition.

TABLE 2

| Capped oligonucleotides | Inhibition of CAT protein expression (%) | |
|---|---|---|
| | 0.03 μM | 0.3 μM |
| Gm8 | 55 | 77 |
| Gm9 | 32 | 88 |
| Gm10 | 69 | 73 |
| Gm11 | 86 | 72 |
| Gm12 | 61 | 82 |
| G8 | 29 | 51 |
| Gm12 (S) (for comparison) | 99 | 100 |
| Gm13 | 23 | <5 |

As explained, a protein expression of an influenza virus can be inhibited by the pharmaceutical composition of the present invention for treating or preventing influenza. Further, the novel capped oligonucleotide of the present invention can provide an extremely effective anti-influenza agent.

As above, the present invention was explained with reference to particular embodiments, but modifications and improvements obvious to those skilled in the art are included in the scope of the present invention.

Free Text in Sequence Listing

Base sequences of SEQ ID NO: 1 to 6 are capable of binding to the PB2 protein which is a subunit of an influenza virus RNA polymerase.

What we claim is:

1. A capped oligonucleotide of the formula (I):

$$m^7GpppXpY \qquad (I)$$

wherein ppp is a triphopshate bridge, p is a monophosphate bridge, $m^7G$ is a 7-methylguanosine group binding at the 5' end thereof to said ppp, X is a 2'-O-methyl guanosine group or guanosine group, said 2'-O-methyl guanosine group or said guanosine group binds at the 5' end thereof to said ppp, and at the 3' end thereof to said p, and Y is an oligoribonucleotide moiety consisting of the base sequence of SEQ ID NO: 4.

2. A composition comprising a capped oligonucleotide of the formula (I), $$m^7GpppXpY \qquad (I)$$

wherein ppp is a triphosphate bridge, p is a monophosphate bridge, $m^7G$ is a 7-methylguanosine group binding at the 5' end thereof to said ppp, X is a 2'-O-methyl guanosine group or guanosine group, said 2'-O-methyl guanosine group or said guanosine group binds at the 5' end thereof to said ppp, and at the 3' end thereof to said p, and Y is an oligoribonucleotide moiety consisting of the base sequence of SEQ ID NO: 4 and binding at the 5' end thereof to said p, and a pharmaceutically acceptable carrier or diluent.

3. A capped oligonucleotide of the formula (I):

$$m^7GpppXpY \qquad (I)$$

wherein ppp is a triphopshate bridge, p is a monophosphate bridge, $m^7G$ is a 7-methylguanosine group binding at the 5' end thereof to said ppp, X is a 2'-O-methyl guanosine group or guanosine group, said 2'-O-methyl guanosine group or said guanosine group binds at the 5' end thereof to said ppp, and at the 3' end thereof to said p, and Y is an oligoribonucleotide moiety consisting of the base sequence of SEQ ID NO: 5.

4. A composition comprising a capped oligonucleotide of the formula (I), $$m^7GpppXpY \qquad (I)$$

wherein ppp is a triphosphate bridge, p is a monophosphate bridge, $m^7G$ is a 7-methylguanosine group binding at the 5' end thereof to said ppp, X is a 2'-O-methyl guanosine group or guanosine group, said 2'-O-methyl guanosine group or said guanosine group binds at the 5' end thereof to said ppp, and at the 3' end thereof to said p, and Y is an oligoribonucleotide moiety consisting of the base sequence of SEQ ID NO: 5 and binding at the 5' end thereof to said p, and a pharmaceutically acceptable carrier or diluent.

* * * * *

SEQUENCE LISTING

```
<160> NUMBER OF SEQ ID NOS: 18

<210> SEQ ID NO 1
<211> LENGTH: 7
<212> TYPE: RNA
<213> ORGANISM: Artificial Sequence
<220> FEATURE:
<223> OTHER INFORMATION: A base sequence capable of binding to PB2
      protein which is a sub unit of influenza virus RNA polymerase

<400> SEQUENCE: 1 aauacuc                                                                    7

<210> SEQ ID NO 2
<211> LENGTH: 8
<212> TYPE: RNA
<213> ORGANISM: Artificial Sequence
<220> FEATURE:
<223> OTHER INFORMATION: A base sequence capable of binding to PB2
      protein which is a sub unit of influenza virus RNA polymerase

<400> SEQUENCE: 2 aauacuca                                                                   8

<210> SEQ ID NO 3
<211> LENGTH: 9
<212> TYPE: RNA
<213> ORGANISM: Artificial Sequence
<220> FEATURE:
<223> OTHER INFORMATION: A base sequence capable of binding to PB2
      protein which is a sub unit of influenza virus RNA polymerase

<400> SEQUENCE: 3 aauacucaa                                                                  9

<210> SEQ ID NO 4
<211> LENGTH: 10
<212> TYPE: RNA
<213> ORGANISM: Artificial Sequence
<220> FEATURE:
<223> OTHER INFORMATION: A base sequence capable of binding to PB2
      protein which is a sub unit of influenza virus RNA polymerase
```

```
<400> SEQUENCE: 4
aauacucaaa                                                          10

<210> SEQ ID NO 5
<211> LENGTH: 11
<212> TYPE: RNA
<213> ORGANISM: Artificial Sequence
<220> FEATURE:
<223> OTHER INFORMATION: A base sequence capable of binding to PB2
      protein which is a sub unit of influenza virus RNA polymerase

<400> SEQUENCE: 5
aauacucaaa c                                                        11

<210> SEQ ID NO 6
<211> LENGTH: 12
<212> TYPE: RNA
<213> ORGANISM: Artificial Sequence
<220> FEATURE:
<223> OTHER INFORMATION: A base sequence capable of binding to PB2
      protein which is a sub unit of influenza virus RNA polymerase

<400> SEQUENCE: 6
aauacucaaa cu                                                       12

<210> SEQ ID NO 7
<211> LENGTH: 25
<212> TYPE: DNA
<213> ORGANISM: Artificial Sequence
<220> FEATURE:
<223> OTHER INFORMATION: 8-TOP: Template DNA for the capped
      oligonucleotides Gm8 and G8 - plus strand

<400> SEQUENCE: 7
taatacgact cactatagaa tactc                                         25

<210> SEQ ID NO 8
<211> LENGTH: 25
<212> TYPE: DNA
<213> ORGANISM: Artificial Sequence
<220> FEATURE:
<223> OTHER INFORMATION: 8-BTM: Template DNA for the capped
      oligonucleotides Gm8 and G8 - minus strand

<400> SEQUENCE: 8
gagtattcta tagtgagtcg tatta                                         25

<210> SEQ ID NO 9
<211> LENGTH: 26
<212> TYPE: DNA
<213> ORGANISM: Artificial Sequence
<220> FEATURE:
<223> OTHER INFORMATION: 9-TOP: Template DNA for the capped
      oligonucleotide Gm9 - plus strand

<400> SEQUENCE: 9
taatacgact cactatagaa tactca                                        26

<210> SEQ ID NO 10
<211> LENGTH: 26
<212> TYPE: DNA
<213> ORGANISM: Artificial Sequence
<220> FEATURE:
<223> OTHER INFORMATION: 9-BTM: Template DNA for the capped
      oligonucleotide Gm9 - minus strand
```

-continued

```
<400> SEQUENCE: 10
tgagtattct atagtgagtc gtatta                                      26

<210> SEQ ID NO 11
<211> LENGTH: 27
<212> TYPE: DNA
<213> ORGANISM: Artificial Sequence
<220> FEATURE:
<223> OTHER INFORMATION: 10-TOP: Template DNA for the capped
      oligonucleotide Gm10 - plus strand

<400> SEQUENCE: 11
taatacgact cactatagaa tactcaa                                     27

<210> SEQ ID NO 12
<211> LENGTH: 27
<212> TYPE: DNA
<213> ORGANISM: Artificial Sequence
<220> FEATURE:
<223> OTHER INFORMATION: 10-BTM: Template DNA for the capped
      oligonucleotide Gm10 - minus strand

<400> SEQUENCE: 12
ttgagtattc tatagtgagt cgtatta                                     27

<210> SEQ ID NO 13
<211> LENGTH: 28
<212> TYPE: DNA
<213> ORGANISM: Artificial Sequence
<220> FEATURE:
<223> OTHER INFORMATION: 11-TOP: Template DNA for the capped
      oligonucleotide Gm11 - plus strand

<400> SEQUENCE: 13
taatacgact cactatagaa tactcaaa                                    28

<210> SEQ ID NO 14
<211> LENGTH: 28
<212> TYPE: DNA
<213> ORGANISM: Artificial Sequence
<220> FEATURE:
<223> OTHER INFORMATION: 11-BTM: Template DNA for the capped
      oligonucleotide Gm11 - minus strand

<400> SEQUENCE: 14
tttgagtatt ctatagtgag tcgtatta                                    28

<210> SEQ ID NO 15
<211> LENGTH: 29
<212> TYPE: DNA
<213> ORGANISM: Artificial Sequence
<220> FEATURE:
<223> OTHER INFORMATION: 12-TOP: Template DNA for the capped
      oligonucleotide Gm12 - plus strand

<400> SEQUENCE: 15
taatacgact cactatagaa tactcaaac                                   29

<210> SEQ ID NO 16
<211> LENGTH: 29
<212> TYPE: DNA
<213> ORGANISM: Artificial Sequence
<220> FEATURE:
<223> OTHER INFORMATION: 12-BTM: Template DNA for the capped
      oligonucleotide Gm12 - minus strand

<400> SEQUENCE: 16
```

```
gtttgagtat tctatagtga gtcgtatta                                    29

<210> SEQ ID NO 17
<211> LENGTH: 30
<212> TYPE: DNA
<213> ORGANISM: Artificial Sequence
<220> FEATURE:
<223> OTHER INFORMATION: 13-TOP: Template DNA for the capped
      oligonucleotide Gm13 - plus strand

<400> SEQUENCE: 17
taatacgact cactatagaa tactcaaact                                   30

<210> SEQ ID NO 18
<211> LENGTH: 30
<212> TYPE: DNA
<213> ORGANISM: Artificial Sequence
<220> FEATURE:
<223> OTHER INFORMATION: 13-BTM: Template DNA for the capped
      oligonucleotide Gm13 - minus strand

<400> SEQUENCE: 18
agtttgagta ttctatagtg agtcgtatta                                   30
```